US008211663B2

(12) United States Patent
Dallmier et al.

(10) Patent No.: US 8,211,663 B2
(45) Date of Patent: Jul. 3, 2012

(54) METHOD FOR MAKING A BIOLOGICAL INDICATOR FOR USE WITH VAPOROUS MICROBIAL DEACTIVATING AGENTS

(75) Inventors: Anthony W. Dallmier, Concord, OH (US); Christopher W. Fisher, Mentor-on-the-Lake, OH (US); Timothy J. Millett, Mentor, OH (US)

(73) Assignee: American Sterilizer Company, Mentor, OH (US)

( * ) Notice: Subject to any disclaimer, the term of this patent is extended or adjusted under 35 U.S.C. 154(b) by 371 days.

(21) Appl. No.: 12/539,947

(22) Filed: Aug. 12, 2009

(65) Prior Publication Data

US 2009/0305334 A1    Dec. 10, 2009

Related U.S. Application Data

(62) Division of application No. 11/679,208, filed on Feb. 27, 2007, now abandoned.

(51) Int. Cl.
*C12Q 1/22*    (2006.01)
(52) U.S. Cl. ........................................ 435/31; 435/287.1
(58) Field of Classification Search .................. None
See application file for complete search history.

(56) References Cited

U.S. PATENT DOCUMENTS

| | | | |
|---|---|---|---|
| 3,925,159 A | 12/1975 | Steiger | 435/242 |
| 5,405,580 A | 4/1995 | Palmer | 422/8 |
| 5,498,526 A | 3/1996 | Caputo et al. | 435/31 |
| 5,516,648 A | 5/1996 | Malchesky et al. | 435/31 |
| 5,552,320 A | 9/1996 | Smith | 435/287.4 |
| 5,856,118 A | 1/1999 | Dalmasso | 435/31 |
| 5,872,004 A | 2/1999 | Bolsen | 435/287.4 |
| 5,942,408 A | 8/1999 | Christensen et al. | 435/31 |
| 6,267,242 B1 | 7/2001 | Nagata et al. | 206/459.1 |
| 6,635,439 B2 | 10/2003 | Morrison et al. | 438/28 |
| 2002/0119508 A1 | 8/2002 | Morrison et al. | 435/27 |

FOREIGN PATENT DOCUMENTS

WO    WO 00/65344    11/2000

OTHER PUBLICATIONS

Joyce E. et al. The development and evaluation of ultrasound for the treatment of bacterial suspensions. A study of frequency, power and sonication time on cultured *Bacillus* species, Ultrasonics Sonochemistry, (2003), vol. 10, pp. 315-318.*
Steris Corporation Website, "VHP® Validation Products," http://www.steris.com/explore/view_product_page.cfm?productid=1062, (last date accessed Aug. 8, 2006).
SGM Biotech, Inc. Website, "SGMStrip™ Spore Strip Biological Indicator," http://www.sgmbiotech.com/products/sgmstrip.php, (last date accessed Aug. 8, 2006).
SGM Biotech, Inc. Website, "Hydrogen Peroxide Vapor Biological Indicators," http://www.sgmbiotech.com/products/vhp.php, (last date accessed Aug. 8, 2006).
The terms "Conform" and "Enclose"—definition from the Merriam-Webster online dictionary, pp. 1-2 for each term, accessed online on May 15, 2009, entire documents.
Brar S.K. et al., Review-Recent advances in downstream processing and formulations of *Bacillus thuingiensis* based biopepsteides, Process Biochemistry, 2006, vol. 41, pp. 323-342, entire document.

* cited by examiner

*Primary Examiner* — Jon P Weber
*Assistant Examiner* — Satyendra Singh
(74) *Attorney, Agent, or Firm* — Kusner & Jaffe; Michael A. Centanni

(57) ABSTRACT

A biological indicator and method of making same. The biological indicator includes a carrier having a recess formed therein in order to restrict movement of an inoculum deposited onto the carrier. The inoculum includes microorganisms (e.g., bacterial spores) suspended in a suspension medium. The microorganisms are prepared by removing extraneous material and subjecting the microorganisms to sonication to break up agglomerations. The suspension medium includes a wetting agent to reduce surface tension, thereby facilitating flow of the suspension medium to prevent stacking of microorganisms on the surface of the carrier, and to allow the inoculum to more evenly "plate out" on carrier surfaces. The carrier, with inoculum deposited thereon, is enclosed in an envelope made of a material permeable to a vaporous deactivating agent (e.g., vaporized hydrogen peroxide, ozone, chlorine dioxide, ethylene oxide, etc.), thereby facilitating exposure to the vaporous deactivating agent.

15 Claims, 1 Drawing Sheet

METHOD FOR MAKING A BIOLOGICAL INDICATOR FOR USE WITH VAPOROUS MICROBIAL DEACTIVATING AGENTS

RELATED APPLICATIONS

This application is a divisional of U.S. application Ser. No. 11/679,208, filed Feb. 27, 2007, now abandoned and is hereby fully incorporated herein by reference.

FIELD OF THE INVENTION

The present invention relates to a biological indicator for determining the efficacy of a microbial deactivation process.

BACKGROUND OF THE INVENTION

Many articles (e.g., medical instruments and devices) and enclosed regions of a wide range of facilities (e.g., medical treatment and research facilities, pharmaceutical manufacturing facilities, animal research facilities, laboratories, patient rooms, hotel rooms, offices, cruise ships, recreational facilities and vehicles) are treated with a vaporous deactivating agent (e.g., vaporized hydrogen peroxide) in a microbial deactivation process to deactivate microbial contamination on the articles or contaminated surfaces within the enclosed region. In order to determine whether the treated articles or enclosed regions have been successfully deactivated, and thereby safe for use, it is necessary to determine whether all of the parameters necessary for deactivation were met during the deactivation process or are present within the enclosed region during the microbial deactivation process. To this end, biological indicators accompany the articles, or are located within the enclosed region, throughout the microbial deactivation process. A typical biological indicator includes a known number of microorganisms (usually bacterial spores) of known resistance to the mode of deactivation, located in or on a carrier (also referred to as a "coupon" or "strip"), and enclosed in a protective package. Before the microorganisms are deposited onto the carrier, the microorganisms are typically suspended in a suspension medium. Subsequent growth or failure of the microorganisms to grow, i.e., after the deactivation process, under suitable conditions indicates the efficacy of the microbial deactivation process.

Known biological indicators include a carrier formed of a metal, such as stainless steel. The carrier has a uniform flat surface on one side of the carrier, upon which microorganisms are deposited. The carrier is typically enclosed within the protective package having one side formed of a material permeable to a vaporous deactivating agent (e.g., Tyvek®) and having the other side formed of a material impermeable to the vaporous deactivating agent (e.g., Mylar®). The carrier is oriented within the package such that the side of the carrier having the microorganisms thereon faces the permeable side of the package, while the opposite side of the carrier faces the impermeable side of the package.

One problem with known biological indicators is that microorganisms become "stacked" on the surface of the carrier, thereby shielding some of the microorganisms from exposure to the vaporous deactivating agent. FIG. 1 illustrates a prior art biological indicator 70 comprised of a carrier 72 having microorganisms 78 suspended within a suspension medium 76. Suspension medium 76 is deposited onto the flat upper surface of carrier 72. As shown in FIG. 1, microorganisms 78 are "stacked" within suspension medium 76 due to suspension medium 76 failing to more evenly distribute across the upper surface of carrier 72.

Still another problem encountered with known biological indicators is that microorganisms disposed on the flat upper surface of the carrier come into contact with the package enclosing the carrier. As a result, microorganisms can be removed from the carrier. Once removed from the carrier, microorganisms may migrate to the opposite side of the carrier facing the impermeable packaging. As a result, the microorganisms may be "masked" from the deactivation process.

Yet another problem with known biological indicators is that the carrier may shift positions within the protective package, thereby causing the side of the carrier having microorganisms deposited thereon to face the impermeable side of the protective package. Accordingly, exposure of the microorganisms to the vaporous deactivating agent is inhibited.

The problems described above result in a biological indicator that does not accurately indicate the efficacy of a microbial deactivation process.

The present invention overcomes these and other problems by providing an improved biological indicator for determining the efficacy of a microbial deactivation process using a vaporous deactivating agent, and a method for making said biological indicator.

SUMMARY OF THE INVENTION

In accordance with one aspect of the present invention, there is provided a biological indicator for determining the efficacy of a microbial deactivation process used to deactivate items by exposing said items to a vaporous deactivating agent, said biological indicator comprising: a carrier having a recess formed therein; and an inoculum including microorganisms suspended in a suspension medium, wherein the inoculum is deposited in the recess.

In accordance with another aspect of the present invention, there is provided a method of making a biological indicator comprised of a carrier and an inoculum including microorganisms suspended in a suspension medium, the biological indicator determining the efficacy of a deactivation process used to deactivate articles by exposing said articles to a vaporous deactivating agent, said method comprising the steps of: (a) cleaning the carrier using a cleaning agent including a detergent; (b) removing extraneous material from said microorganisms; (c) exposing said microorganisms to ultrasonic vibrations to break up agglomerations of said microorganisms; (d) suspending said microorganisms in the suspension medium to form the inoculum; and (e) depositing said inoculum onto said carrier.

An advantage of the present invention is the provision of a biological indicator having an inoculum with minimal extraneous material therein.

Another advantage of the present invention is the provision of a biological indicator having a suspension medium that minimizes stacking of microorganisms.

Still another advantage of the present invention is the provision of a biological indicator having a carrier dimensioned to inhibit migration of inoculum.

Still another advantage of the present invention is the provision of a biological indicator having a carrier formed of a material compatible with an oxidative vaporous microbial deactivating agent.

Still another advantage of the present invention is the provision of a biological indicator having a protective packaging with improved permeability for vaporous microbial deactivating agents.

Yet another advantage of the present invention is the provision of a method for making the above-mentioned biological indicator.

Yet another advantage of the present invention is the provision of a method of making a biological indicator that minimizes agglomeration of microorganisms.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof and wherein.

DETAILED DESCRIPTION OF A PREFERRED EMBODIMENT

It should be understood that as used herein the term "vaporous" deactivating agents also includes "gaseous" deactivating agents. By way of example, and not limitation, the deactivating agents may include vaporized hydrogen peroxide, ozone, chlorine dioxide, and ethylene oxide.

Figure 2:
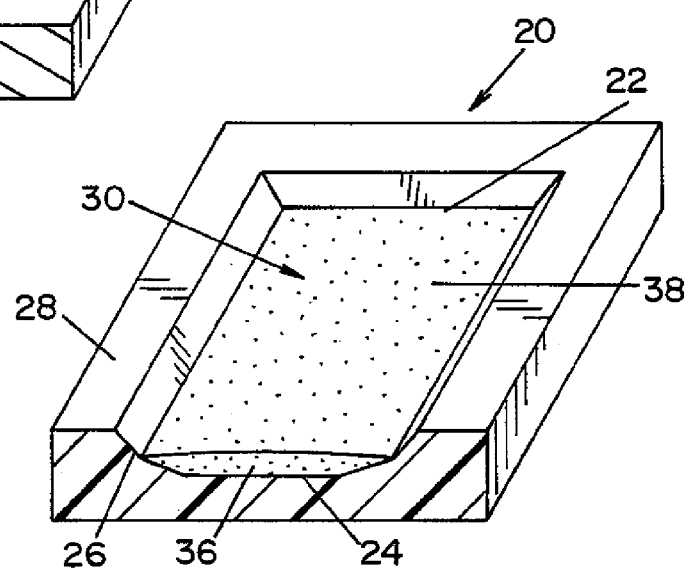
FIG. 2 is a perspective cutaway view of a carrier for a biological indicator according to an embodiment of the present invention.
Figure 3:
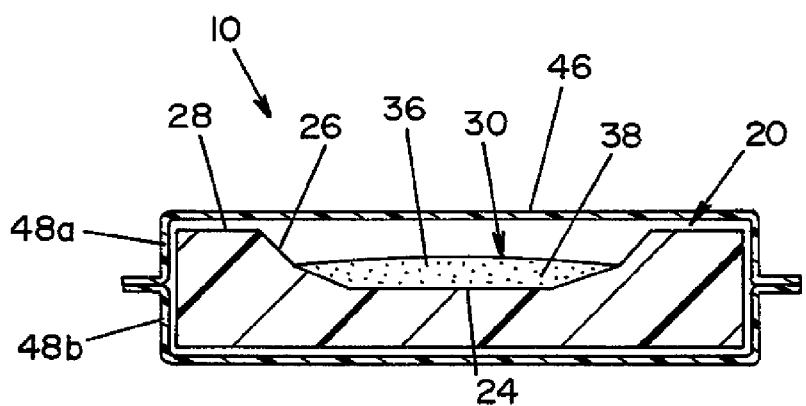
FIG. 3 is a cross-sectional view of a biological indicator according to an embodiment of the present invention, said biological indicator including a carrier, inoculum and packaging.

Referring now to the drawings wherein the showings are for the purpose of illustrating a preferred embodiment of the invention only, and not for the purpose of limiting same, FIG. 3 shows a biological indicator (BI) 10 according to an embodiment of the present invention. BI 10 is generally comprised of a carrier 20 (best seen in FIG. 2); an inoculum 30 comprised of a plurality of microorganisms 38 suspended in a suspension medium 36; and an envelope 46. Inoculum 30 is prepared by suspending microorganisms 38 within suspension medium 36. Inoculum 30 is deposited onto carrier 20. Thereafter, carrier 20 is sealed within envelope 46. Each component of BI 10 is described in detail below.

In the illustrated embodiment, carrier 20 is a generally planar plate or strip having a cavity or recess 22 formed on one side thereof, as best seen in FIG. 2. Recess 22 is defined by a generally planar bottom surface 24 and a plurality of side walls 26 surrounding bottom surface 24. Side walls 26 slope upward from bottom surface 24 to a generally planar upper surface 28 that is disposed around the periphery of recess 22. Recess 22 is dimensioned to receive inoculum 30, comprised of microorganisms 38 suspended in a suspension medium 36.

Carrier 20 is preferably formed of a polymeric material such as polypropylene, polyethylene, polyvinyl-carbonate, polyvinyl styrene, polyvinyl chloride, polyethylene terephthalate, nylon, epoxy, or a mixture of polymeric materials. It is also contemplated that carrier 20 may be formed of a metal (such as aluminum or stainless steel) or a ceramic. However, carrier 20 is preferably formed of a polymeric material since polymeric materials do not oxidize in the presence of oxidizing vaporous microbial deactivating agents, such as vaporized hydrogen peroxide; provide flexibility to allow a wide variety of shapes for carrier 20; and are relatively inexpensive.

In a preferred embodiment, suspension medium 36 of inoculum 30 is an aqueous solution comprising an oxidant-compatible surfactant. Suitable surfactants include, but are not limited to, Triton® X-100, Tween® 80 or sodium dodecyl sulfate. The surfactant acts as a wetting agent to reduce surface tension, thereby reducing microorganism "stacking." Suspension medium 36 may also include an alcohol to increase the rate at which suspension medium 36 dries after being deposited into recess 22 of carrier 20. Suitable alcohols include, but are not limited to, ethyl alcohol or iso-propyl alcohol. Reduced surface tension and faster drying allows suspension medium 36, and microorganisms 38 suspended therein, to more easily and readily spread across bottom surface 24 of carrier 20. Increased spreading of inoculum 30 minimizes "stacking" of microorganisms 38 within suspension medium 36.

In the illustrated embodiment, microorganisms 38 of inoculum 30 are bacterial spores, including, but not limited to, the following: *Geobacillus stearothermophilus, Bacillus atrophaeus, B. pumitus, C. sporogenes*, and combinations thereof. It should be understood that microorganisms 38 are not limited to bacterial spores, and thus may include bacteria (such as *Staphylococcus aureus, Salmonella choleraesuis* and *Pseudomonas aeruginosa*), fungi (such as *Tricophyton mentagrophytes*), and viruses.

In the illustrated embodiment, envelope 46 is comprised of two generally flexible, planar sheets 48a and 48b. Sheets 48a, 48b are attached to each other along their perimeters (e.g., by an adhesive or by heat sealing). Envelope 46, formed by sheets 48a and 48b, is dimensioned to enclose carrier 20. In the illustrated embodiment sheets 48a, 48b are both formed of a material permeable to vaporous deactivating agents, such as vaporized hydrogen peroxide, but generally impermeable to microorganisms, such as bacterial spores. Preferably, sheets 48a, 48b are formed of a nonwoven polymer material, such as an olefin that is spun-bonded. A suitable spun-bonded olefin material is commercially available from Dow Chemical as Tyvek®. In one embodiment of the present invention, sheets 48a, 48b are formed of 2FS Tyvek®. By way of example and not limitation, sheets 48a, 48b may also be formed of one of the following materials: 1073B Tyvek®, other Tyvek® products, non-woven polymers, olefins, polyester film, and a combination thereof. However, 2FS Tyvek® is a preferred material due to its permeability with respect to vaporous deactivating agents.

Preparation of the surfaces of carrier 20 in advance of depositing inoculum 30 thereon will now be described. Carrier 20 is prepared as follows: during a cleaning step, carrier 20 is exposed to a cleaning agent for a predetermined period of time. Preferably, the cleaning agent includes an enzymatic detergent, such as STERIS Klenzyme® detergent, available from STERIS Corporation of Mentor, Ohio. The purpose of the cleaning step is to remove oils (e.g., casting oils), organics, dirt and other contaminants from the surface of carrier 20, thereby reducing oxidant demand during a microbial deactivating process. In this regard, contaminants, such as oil, can be oxidized by a vaporous decontaminating agent (e.g., vaporized hydrogen peroxide), thus reducing the amount of vaporous deactivating agent acting upon the target microorganisms 38.

Following the cleaning step, carrier 20 is exposed to a rinsing fluid for removal of any residual materials remaining on the surfaces of carrier 20, such as residual cleaning agent. In one embodiment, the rinsing fluid includes an alcohol such as ethyl or isopropyl alcohol.

Prior to suspension within suspension medium 36, microorganisms 38 undergo a "washing" procedure to remove extraneous material therefrom. By way of example, but not limitation, the extraneous material may include cellular debris, excess organic material, growth media, and "spent" microorganisms 38. Removal of extraneous material from microorganisms 38 also reduces oxidant demand during a microbial deactivating process. As a result, a greater amount of the vaporous deactivating agent can act upon the target microorganisms 38. It should be understood that dyes are preferably omitted from suspension medium 36 to reduce oxidative demand during a microbial deactivating process, since dyes are also inherently prone to oxidative attack.

As indicated above, removing contaminants from the surfaces of carrier 20, removing extraneous materials from microorganisms 38 prior to deposition onto carrier 20, and eliminating dyes from suspension medium 36, minimizes the oxidative demand from materials other than microorganisms 38. Accordingly, a greater amount of the oxidative vaporous deactivating agent is available to act on microorganisms 38 within suspension medium 36. As a result, the accuracy of BI 10 is improved.

Prior to suspension within suspension medium 36, microorganisms 38 also undergo a "mild" sonication (e.g., ultrasonic vibrations) to minimize agglomeration (i.e., "clumping") of microorganisms 38. Reduction of agglomeration improves the ability of microorganisms 38 to flow or spread across bottom surface 24 of carrier 20 when inoculum 30 is deposited in recess 22.

After suspension medium 38 and microorganisms 36 have been prepared as described above, inoculum 30 is formed by suspending microorganisms 36 in suspension medium 38.

Following preparation of inoculum 30 and carrier 20, as described above, inoculum 30 is deposited into recess 22 of carrier 20. Inoculum 30 spreads out across bottom surface 24 due to the reduced surface tension provided by the surfactant. Side walls 26 maintain inoculum 30 within recess 22, thereby preventing migration of inoculum 30 onto upper surface 28. Side walls 26 also prevent inoculum 30 from becoming removed from carrier 20 or from migrating onto the inner surfaces of envelope 46. In addition, side walls 26 minimize "drop formation" by causing inoculum 30 to plate out on side walls 26. Recess 22 allows faster production of BI 10, since migration of inoculum 30 is inhibited.

Figure 1:
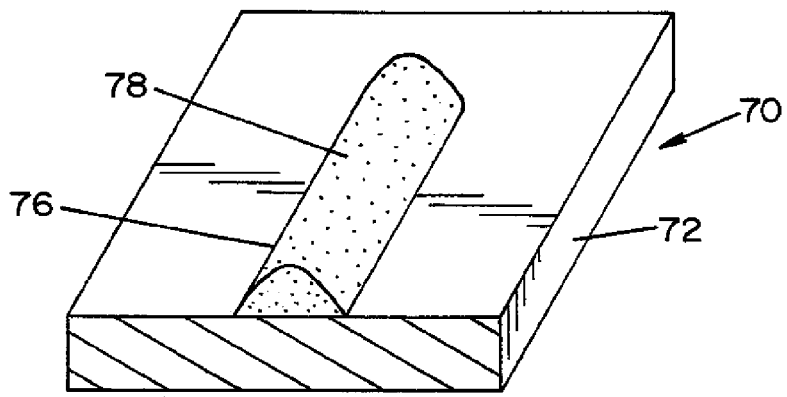
FIG. 1 is a perspective cutaway view of a carrier of a prior art biological indicator.

As indicated above, the reduced surface tension of suspension medium 36 facilitates the spreading of inoculum 30 across the area of bottom surface 24. As a result, microorganisms 38 are spread across a larger surface area than with prior art BI 70, thereby minimizing stacking of microorganisms 38. Less stacking of microorganisms 38 results in improved exposure of microorganisms 38 to the vaporous deactivating agent. In this regard, when microorganisms 38 are stacked (see FIG. 1), microorganisms 38 located at the top of the stack block microorganisms 38 located below. The blocked microorganisms 38 thus fail to be properly exposed to the vaporous deactivating agent. As a result, the accuracy of the biological indicator can be impaired.

The presence of the alcohol in suspension medium 36 allows for fast drying of inoculum 30 after deposition into recess 22, thereby minimizing opportunities for unwanted migration of inoculum 30 during handling of BI 10. The presence of alcohol also reduces surface tension, thereby providing the advantages described above.

After inoculum 30 has dried on bottom surface 24 of carrier 20, carrier 20 is sealed inside envelope 46. As indicated above, sheets 48a, 48b are preferably formed of a material permeable to the vaporous deactivating agent (e.g., vaporized hydrogen peroxide), but impermeable to microorganisms 38.

Operation of BI 10 will now be described with reference to the deactivation of articles within a deactivation chamber. BI 10 is placed within the deactivation chamber along with articles that are to be subject to a microbial deactivation process. The articles and BI 10 are exposed to a vaporous deactivating agent (such as vaporized hydrogen peroxide) during the microbial deactivation process.

After the microbial deactivation process is completed, biological indicator 10 is removed from the deactivation chamber and microorganisms 36 are cultured to determine whether any of microorganisms 36 remain viable following the microbial deactivation process. If less than a threshold number of microorganisms 36 remain viable following exposure to the vaporous deactivating agent during the microbial deactivation process, then the microbial deactivation process is considered to have been effective.

The foregoing is one embodiment of the present invention. It should be appreciated that this embodiment is described for purposes of illustration only, and that those skilled in the art may practice numerous alterations and modifications without departing from the spirit and scope of the invention. It is intended that all such modifications and alterations be included insofar as they come within the scope of the invention as claimed or the equivalents thereof.

Having described the invention, the following is claimed:

1. A method of making a biological indicator comprised of a carrier and an inoculum including bacterial spores suspended in a suspension medium, the biological indicator determining the efficacy of a deactivation process used to deactivate articles by exposing said articles to a vaporous deactivating agent, said method comprising the steps of:
   cleaning the carrier using a cleaning agent including a detergent;
   removing extraneous material from said bacterial spores;
   exposing said bacterial spores to ultrasonic vibrations prior to suspension within said suspension medium to break up agglomerations of said bacterial spores;
   suspending said bacterial spores in the suspension medium to form the inoculum; and
   depositing said inoculum into said carrier.

2. A method of making a biological indicator as defined in claim 1, wherein said step of removing extraneous material from said bacterial spores includes washing said bacterial spores.

3. A method of making a biological indicator as defined in claim 1, wherein said suspension medium includes a wetting agent.

4. A method of making a biological indicator as defined in claim 3, wherein said wetting agent is a surfactant compatible with said vaporous deactivating agent.

5. A method of making a biological indicator as defined in claim 1, wherein said suspension medium includes an alcohol.

6. A method of making a biological indicator as defined in claim 1, wherein said method further comprises:
   enclosing said carrier having inoculum deposited thereon in an envelope made of a material permeable to said vaporous deactivating agent and generally impermeable to said bacterial spores.

7. A method of making a biological indicator as defined in claim 6, wherein said material includes a spun-bonded olefin.

8. A method of making a biological indicator as defined in claim 1, wherein said method further comprises the step of:
   rinsing said carrier with a rinsing solution including an alcohol, prior to depositing said inoculum thereon.

9. A method of making a biological indicator as defined in claim 1, wherein said vaporous deactivating agent includes: vaporized hydrogen peroxide, ozone, chlorine dioxide, or ethylene oxide.

10. A method of making a biological indicator as defined in claim 1, wherein said inoculum is deposited into a recess in said carrier, said recess defined by a generally planar bottom surface and a plurality of side walls surrounding said bottom surface, said side walls sloping upward from said bottom surface to a generally planar upper surface that is disposed around the periphery of said recess of said carrier.

11. A method of making a biological indicator as defined in claim 1, wherein said carrier is formed of a polymeric material.

12. A method of making a biological indicator as defined in claim 11, wherein said polymeric material includes at least one of the following: polypropylene, polyethylene, polyvinyl-carbonate, polyvinyl styrene, polyvinyl chlorine, polyethylene terephthalate, nylon, epoxy, or a mixture of polymeric materials.

13. A method of making a biological indicator as defined in claim 1, wherein said carrier is formed of a metal.

14. A method of making a biological indicator as defined in claim 13, wherein said carrier includes at least one of: aluminum or stainless steel.

15. A method of making a biological indicator as defined in claim 1, wherein said carrier is formed of a ceramic.

* * * * *